US 9,878,842 B2

(12) United States Patent
Golgotiu et al.

(10) Patent No.: US 9,878,842 B2
(45) Date of Patent: Jan. 30, 2018

(54) PLANT IMAGING AND SPECTRAL SCANNING SYSTEM AND METHOD

(71) Applicant: Dow AgroSciences LLC, Indianapolis, IN (US)

(72) Inventors: Kirsti A. Golgotiu, Oregon City, OR (US); Brent Allen Gibson, Hubbard, OR (US); Cory A. Christensen, Sherwood, OR (US)

(73) Assignee: Dow AgroSciences LLC, Indianapolis, IN (US)

( * ) Notice: Subject to any disclaimer, the term of this patent is extended or adjusted under 35 U.S.C. 154(b) by 234 days.

(21) Appl. No.: 14/540,464

(22) Filed: Nov. 13, 2014

(65) Prior Publication Data

US 2015/0177067 A1    Jun. 25, 2015

Related U.S. Application Data

(60) Provisional application No. 61/919,841, filed on Dec. 23, 2013.

(51) Int. Cl.
*A01G 7/06* (2006.01)
*B65D 85/52* (2006.01)
*G01N 21/25* (2006.01)
*G01N 21/84* (2006.01)

(52) U.S. Cl.
CPC .............. *B65D 85/52* (2013.01); *A01G 7/06* (2013.01); *G01N 21/255* (2013.01); *G01N 21/84* (2013.01); *G01N 2021/845* (2013.01); *G01N 2021/8466* (2013.01); *G01N 2201/062* (2013.01); *G01N 2201/0634* (2013.01); *G01N 2201/06133* (2013.01)

(58) Field of Classification Search
CPC .... A01G 7/06; B65D 85/52; G01N 2021/845; G01N 2021/8466; G01N 21/255; G01N 21/84; G01N 2201/06133; G01N 2201/062; G01N 2201/0634
USPC .............................. 206/423; 348/89; 356/402
See application file for complete search history.

(56) References Cited

U.S. PATENT DOCUMENTS

| 4,741,042 | A |   | 4/1988  | Throop et al.          |
|-----------|---|---|---------|------------------------|
| 4,839,522 | A |   | 6/1989  | Bourgeois et al.       |
| 4,867,563 | A | * | 9/1989  | Wurm ........ G01J 3/06 |
|           |   |   |         |            356/328     |
| 4,883,542 | A | * | 11/1989 | Voneiff ..... B08B 5/00 |
|           |   |   |         |            134/21      |

(Continued)

FOREIGN PATENT DOCUMENTS

| EP | 1817558 A4     | 2/2012  |
| WO | WO2013/05561 A2 | 4/2013 |
| WO | WO2013186144 A1 | 12/2013 |

OTHER PUBLICATIONS

PSI Plantscreen System Plant Phenotyping by PSI (Photon Systems Instruments); brochure.*

(Continued)

*Primary Examiner* — Mohammed Rahaman
*Assistant Examiner* — James Boylan
(74) *Attorney, Agent, or Firm* — Eric J. Kraus; Faegre Baker Daniels LLP (57) ABSTRACT

A system and method is disclosed for imaging and scanning a plurality of plants to capture information related to plant performance. Plants move through the system on a conveyor belt in specialized plant container pot holders.

39 Claims, 5 Drawing Sheets

(56) References Cited

U.S. PATENT DOCUMENTS

| | | | |
|---|---|---|---|
| 5,253,302 A | 10/1993 | Massen | |
| 5,394,237 A * | 2/1995 | Chang | G01J 3/02 |
| | | | 250/339.02 |
| 5,984,591 A * | 11/1999 | Hilbish | B65G 51/03 |
| | | | 406/88 |
| 6,100,526 A | 8/2000 | Mayes | |
| 6,507,361 B1 * | 1/2003 | Barber | G06T 11/60 |
| | | | 348/207.2 |
| 6,646,264 B1 | 11/2003 | Modiano et al. | |
| 7,123,750 B2 | 10/2006 | Lu et al. | |
| 7,262,858 B2 | 8/2007 | Lin et al. | |
| 7,412,330 B2 | 8/2008 | Spicer et al. | |
| 7,715,013 B2 | 5/2010 | Glaser et al. | |
| 7,830,504 B2 | 11/2010 | Deppermann et al. | |
| 2005/0097021 A1 * | 5/2005 | Behr | G01N 21/85 |
| | | | 705/36 R |
| 2006/0255261 A1 * | 11/2006 | Whitehouse | H01J 49/0431 |
| | | | 250/288 |
| 2006/0283145 A1 * | 12/2006 | Weisgerber | B07C 5/3404 |
| | | | 53/167 |
| 2010/0188561 A1 * | 7/2010 | Knoedgen | H04N 17/00 |
| | | | 348/370 |
| 2011/0135161 A1 * | 6/2011 | Koutsky | A01H 1/04 |
| | | | 382/110 |
| 2013/0113922 A1 * | 5/2013 | Wang | H04N 5/262 |
| | | | 348/135 |
| 2013/0115717 A1 * | 5/2013 | Guo | G01N 33/54346 |
| | | | 436/501 |
| 2013/0141011 A1 * | 6/2013 | Fushimi | H05B 37/02 |
| | | | 315/294 |
| 2013/0296711 A1 * | 11/2013 | Curiel | A61B 5/0077 |
| | | | 600/476 |
| 2015/0156839 A1 * | 6/2015 | Chen | H05B 33/0863 |
| | | | 315/210 |
| 2015/0212229 A1 * | 7/2015 | Walcher | G01V 5/0008 |
| | | | 378/57 |

OTHER PUBLICATIONS

Google screenshot providing/showing the date of the PSI brochure above.*

International Search Report and Written Opinion dated Apr. 14, 2015 from the ISA in related International Application PCT/US2014/069522.

Sahba et al. "Photonics-based Spectral Reflectance Sensor for Plant Discrimination". Optical Internet, 2007 and the 2007 32nd Australian Conference on Optical Fibre Technology. COIN-ACOFT 2007, 2007, pp. 1, 3, 24-27.

Askraba et al. "Design of laser multi-beam generator for plant discrimination". High Capacity Optical Networks and Enabling Technologies (HONET), 2011, pp. 26, 29, 19-21.

Chaerle et al. "Monitoring and Screening Plant Populations with Combined Thermal and Chlorophyll Fluorescence Imaging". Journal of Experimental Botany, 2006, vol. 58 No. 4, pp. 773-784.

* cited by examiner

PLANT IMAGING AND SPECTRAL SCANNING SYSTEM AND METHOD

CROSS REFERENCE TO RELATED APPLICATION

This application claims the benefit of U.S. Provisional Patent Application Ser. No. 61/919,841, filed Dec. 23, 2014, the disclosure of which is expressly incorporated by reference herein.

BACKGROUND AND SUMMARY OF THE DISCLOSURE

The present disclosure relates to a system and method imaging and scanning a plurality of plants to capture information related to plant performance such as when the plants are under abiotic stress, for example.

High throughput screening systems of transgenic candidates in plants such as maize preferably capture data related to plant performance under abiotic stress in a rapid, efficient, yet comprehensive manner. Rapid processing involving logistics of plant container handling, morphological data capture, series control during data capture, and data analysis and management.

The system and method of the present disclosure provides both an imaging booth and a spectral signature capture booth designed for morphological phenotyping through both image capture and hyperspectral scanning of individual plantlets. The illustrated system enables rapid data capture of thousands of plants per imaging or scanning event and integrates into a vegetative stage high throughput screening program.

In an illustrated embodiment, plants are placed in a custom designed pot holder in a loading queue on a gravity feed conveyor system. The conveyor system times the release of each pot holder onto a conveyor belt such that they travel in sequence and are equally spaced from one another. The pot holders travel on the conveyor belt through a highly lighted imaging booth, through a hyperspectral scanning booth, and then out to the unloading queue.

In one illustrated embodiment of the present disclosure, an imaging booth is disclosed for taking images of a plant located within a plant container moving on a conveyor belt through the imaging booth. The imaging booth includes a housing having an entrance opening and an exit opening to permit the plant container to enter and exit the housing on the conveyor belt, respectively. The housing also has a generally planar wall located on a first side of the conveyor belt and an arcuate wall located on a second, opposite side of the conveyor belt. The arcuate wall has a concave shape directed toward the generally planar wall. The imaging booth also includes a plurality of lights located on the arcuate wall to illuminate the plant in the plant container located on the conveyor belt in front of the generally planar wall, and a camera located in the housing above the conveyor belt to capture images of the illuminated plant in the plant container located on the conveyor belt.

In an illustrated embodiment, the arcuate wall has a semi-circular shape. The housing also has a ceiling located above the arcuate wall and the generally planar wall. A plurality of lights are located on the ceiling of the housing to further illuminate the plant located in the plant container on the conveyor belt.

In another illustrated embodiment of the present disclosure, a hyperspectral scanning booth is disclosed for a plant located in a plant container moving through the scanning booth on a conveyor belt. The scanning booth includes a housing having an interior region, an entrance opening and an exit opening to permit the plant containers to enter and exit the housing on the conveyor belt passing through a bottom portion of the housing, at least one high intensity lamp located in the interior region of the housing above the conveyor belt to illuminate the plant located in the plant container on the conveyor belt, and a spectroradiometer probe located in the interior region of the housing above the conveyor belt to capture a reflected spectral signature from the illuminated plant. The scanning booth also includes at least one shield located in the housing above the conveyor belt and below the at least one high intensity lamp and the probe. The at least one shield is configured to obscure the conveyor belt from the probe.

In an illustrated embodiment, first and second shields are located in the housing above the conveyor belt. The first and second shields being aligned generally parallel to the conveyor belt and extend longitudinally from the entrance opening to the exit opening of housing. The first and second shields are separated from each other by a longitudinally extending gap to permit a portion of the plant to pass between the first and second shields with the plant container being located below the first and second shields. In one illustrated embodiment, the first and second shields each include a lead-in ramp surface located adjacent the entrance opening of the housing to guide a portion of plant into the slot between the first and second shields. Therefore, a stalk of the plant extends through the slot between the first and second shields so that leaves of the plant are located above the first and second shields for illumination by the at least one high intensity lamp and for scanning by the probe.

In yet another illustrated embodiment of the present disclosure, a holding apparatus for a plant located within a plant container includes a semi-spherical base having a flat bottom surface and a flange defining a top opening, and an upwardly extending tube coupled to the base. The tube has a first end located in the top opening of the base to secure the tube to the base and a second open end configured to receive the plant container therein.

BRIEF DESCRIPTION OF THE DRAWINGS

The foregoing aspects and many additional features of the present system and method will become more readily appreciated and become better understood by reference to the following detailed description when taken in conjunction with the accompanying drawings.

Corresponding reference characters indicate corresponding parts throughout the several views. Although the drawings represent embodiments of various features and components according to the present disclosure, the drawings are not necessarily to scale and certain features may be exaggerated in order to better illustrate and explain the present disclosure. The exemplification set out herein illustrates embodiments of the invention, and such exemplifications are not to be construed as limiting the scope of the invention in any manner.

DETAILED DESCRIPTION OF THE DRAWINGS

For the purposes of promoting an understanding of the principles of the present disclosure, reference will now be made to the embodiments illustrated in the drawings, which are described below. The embodiments disclosed below are not intended to be exhaustive or limit the invention to the precise form disclosed in the following detailed description. Rather, the embodiments are chosen and described so that others skilled in the art may utilize their teachings. It is understood that no limitation of the scope of the invention is thereby intended. The invention includes any alterations and further modifications in the illustrated devices and described methods and further applications of the principles of the invention which would normally occur to one skilled in the art to which the invention relates.

Figure 1:
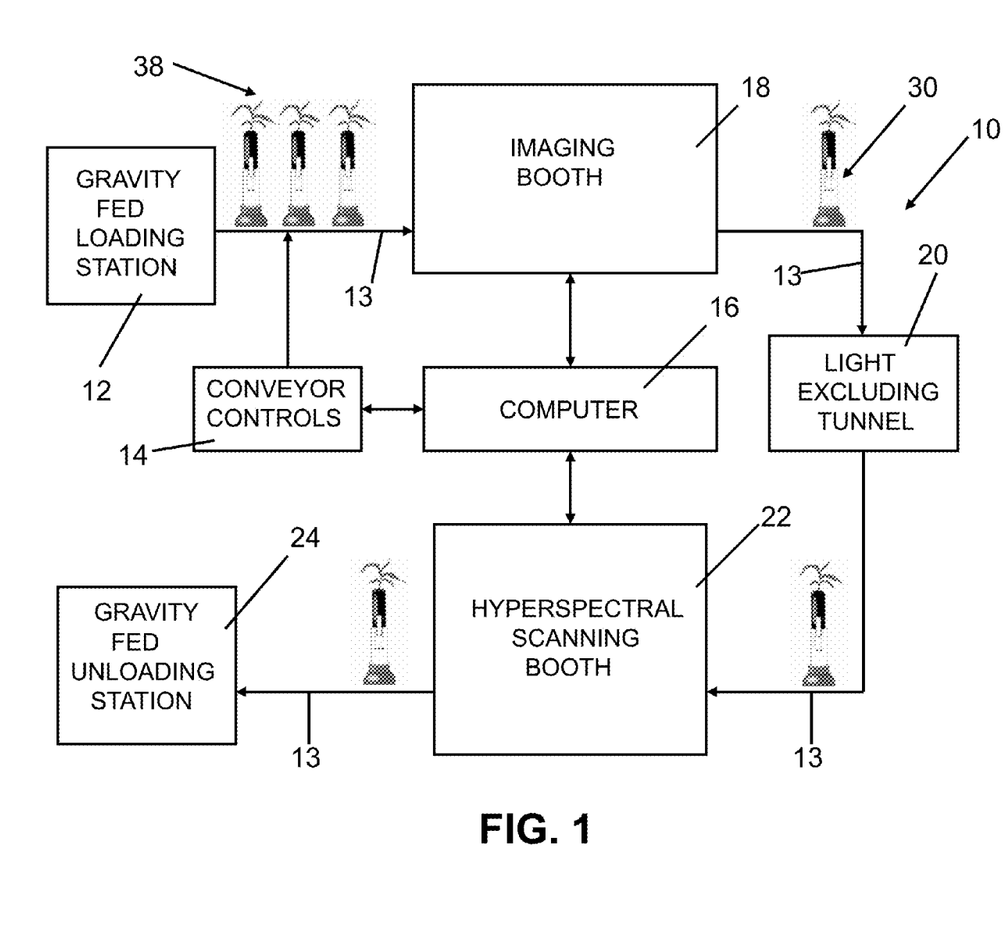
FIG. 1 is a block diagram illustrating a plant imaging and spectral scanning system of an illustrated embodiment of the present disclosure.
Figure 2:
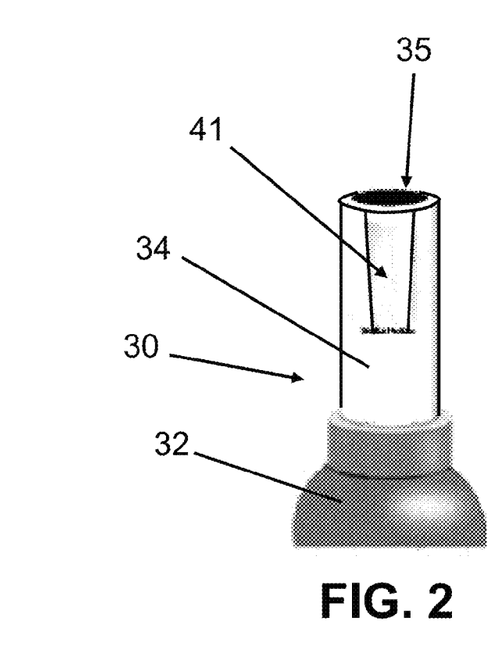
FIG. 2 illustrates a plant pot holder of an illustrated embodiment of the present disclosure for holding plant containers as they pass through the plant imaging and spectral scanning system of FIG. 1 on a conveyor belt.
Figure 3:
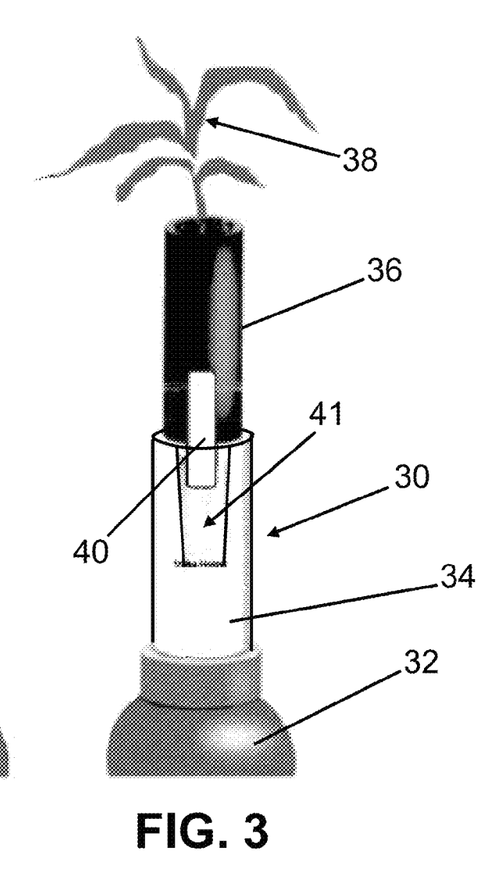
FIG. 3 illustrates the plant pot holder of FIG. 2 with a plant container located therein.

Referring now to the drawings, the present disclosure relates to a system and method for capturing information related to plant performance under abiotic stress in a rapid, efficient and comprehensive manner. The plant imaging and scanning system 10 is illustrated in FIG. 1. Plants 38 located in specialized pot holders 30 discussed below with reference to FIGS. 2 and 3 are first loaded into a gravity fed loading station 12. The pot holders 30 move on a conveyor belt 13 controlled by conveyer controls 14 and computer 16. Conveyer controls 14 provide a timed release of each plant pot holder 30 from loading station 12 onto the conveyer belt 13 using a movable gate 47, arm or other suitable controls.

In an illustrated embodiment, the plants 38 are grown in plant containers 36. Plant containers 36 passing through system 10 are loaded into individual pot holders 30 as best shown in FIGS. 2 and 3. In an illustrated embodiment, each pot holder 30 includes an enlarged semi-spherical base 32 having a flat bottom surface and a flange defining a top opening of the base 32. An upwardly extending tube 34 in located in the top opening of the base 32 to secure the tube 34 to base 32. The base 32 is filled with sand or other heavy material to provide a low center of gravity for stability for the pot holder 30. In an illustrated embodiment, base 32 is an inverted plastic drain and tube 34 is a PVC pipe although other suitable components may be used.

The illustrated pot holders 30 are formed from a three inch (7.6 cm) OD ABS tube 34, cut to approximately eight inches (20.3 cm) in height, and positioned in an inverted ABS plastic floor drain having a six inch diameter (15.2 cm) used as base 32. The weight distribution of the pot holder 30 is primarily in the base 32 at the bottom of the pot holder 30, thereby allowing for easy travel of the pot holder 30 across both the gravity feed loading station 12 and the automated conveyer belt 13. The pot holders 30 are preferably black or blue in color. The black or blue color prevents the holders 30 from affecting the image color analysis discussed below.

Containers 36 holding plants 38 are inserted into the tubes 34 as shown in FIG. 3. The plant pots 30 are then loaded on to the gravity fed loading station 12 for processing. Each plant container 36 includes an identification label 40 which is visible within the images taken by imaging booth 18 confirming an identification of each plant. In one embodiment, labels 40 are held in a transparent sleeve 41 on tube 34 of pot holder 30.

The plants 38 in pot holders 30 first pass into an imaging booth 18 on conveyor belt 13. Imaging booth 18 takes photographic images of each plant 38. The imaging booth 18 is enclosed and includes an intense light source illustratively formed by a panel of flexible LED rope lights on arcuate wall 50 forming a semicircle around the plant 38 as discussed below with reference to FIGS. 4 and 5. A camera 52 is located above plants 38 in the imaging booth 18. The background color on a wall 54 within the imaging booth 18 is preferably blue. The conveyer belt 13 is also preferably blue. The blue color is later excluded in color analysis by publicly available imaging software discussed below.

In an illustrated embodiment, the plants 38 exit the imaging booth 18 and pass through a light excluding tunnel 20 which prevents light from the imaging booth 18 from influencing the hyperspectral scanning booth 22. The tunnel 20 may be omitted if the light from imaging booth 18 does not affect the scanning booth 22.

Next, the plants 38 within pot holders 30 pass through scanning booth 22. Details of the scanning booth 22 are discussed below in connection with FIG. 6. Plant pot holders 30 exiting the scanning booth 22 on conveyor belt 13 enter a gravity fed unloading station 24. Plant containers 36 are then removed from pot holders 30 and placed within other suitable containers on a growth track of an automated bench system. The pot holders 30 are then returned for receiving another plant container 36 and placement on the gravity fed loading station 12 for the next imaging and scanning cycle.

Figure 4:
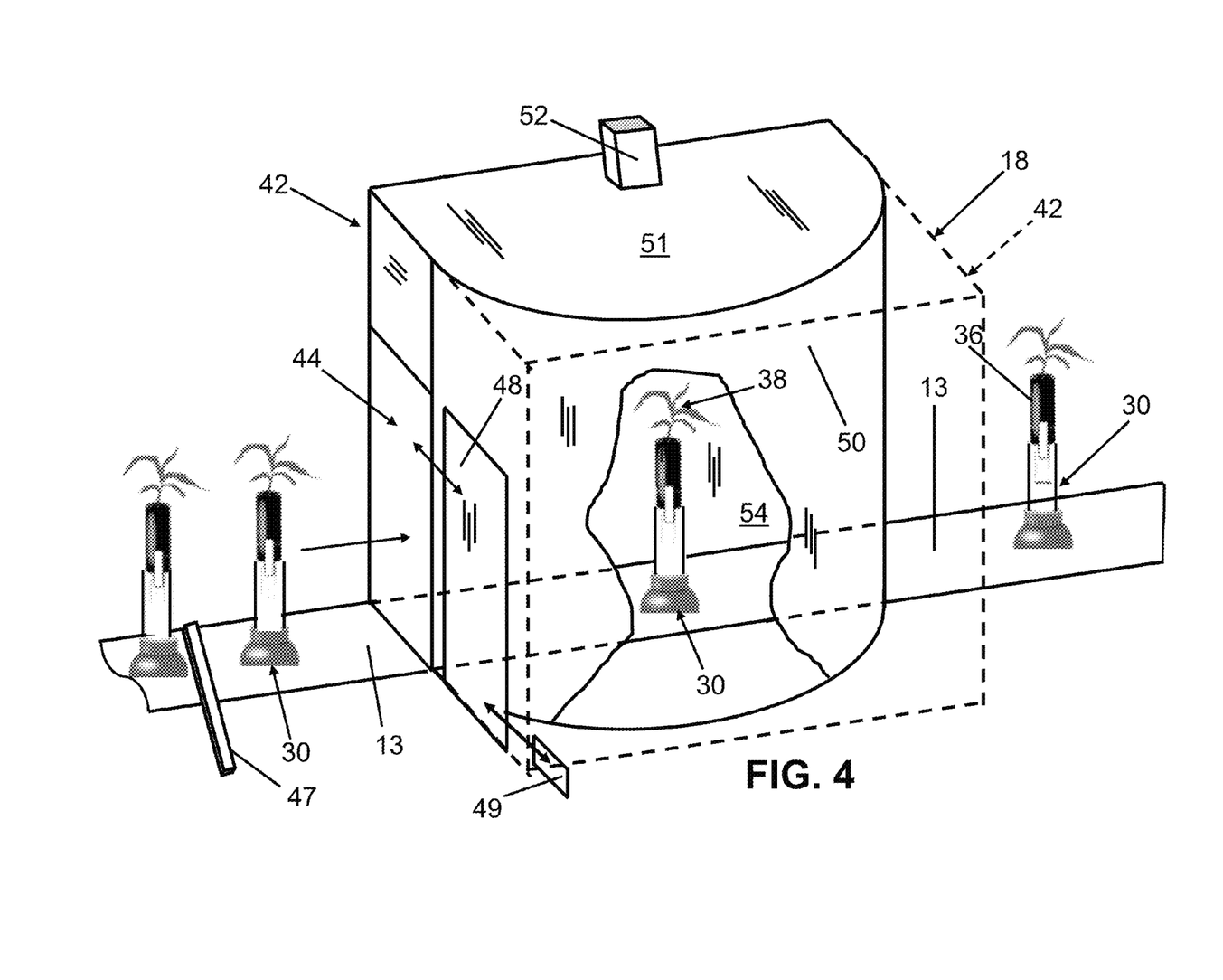
FIG. 4 is a perspective view illustrating details of an imaging booth for capturing images of the plants as the plants move through the imaging booth in the plant pot holder on the conveyor belt.
Figure 5:
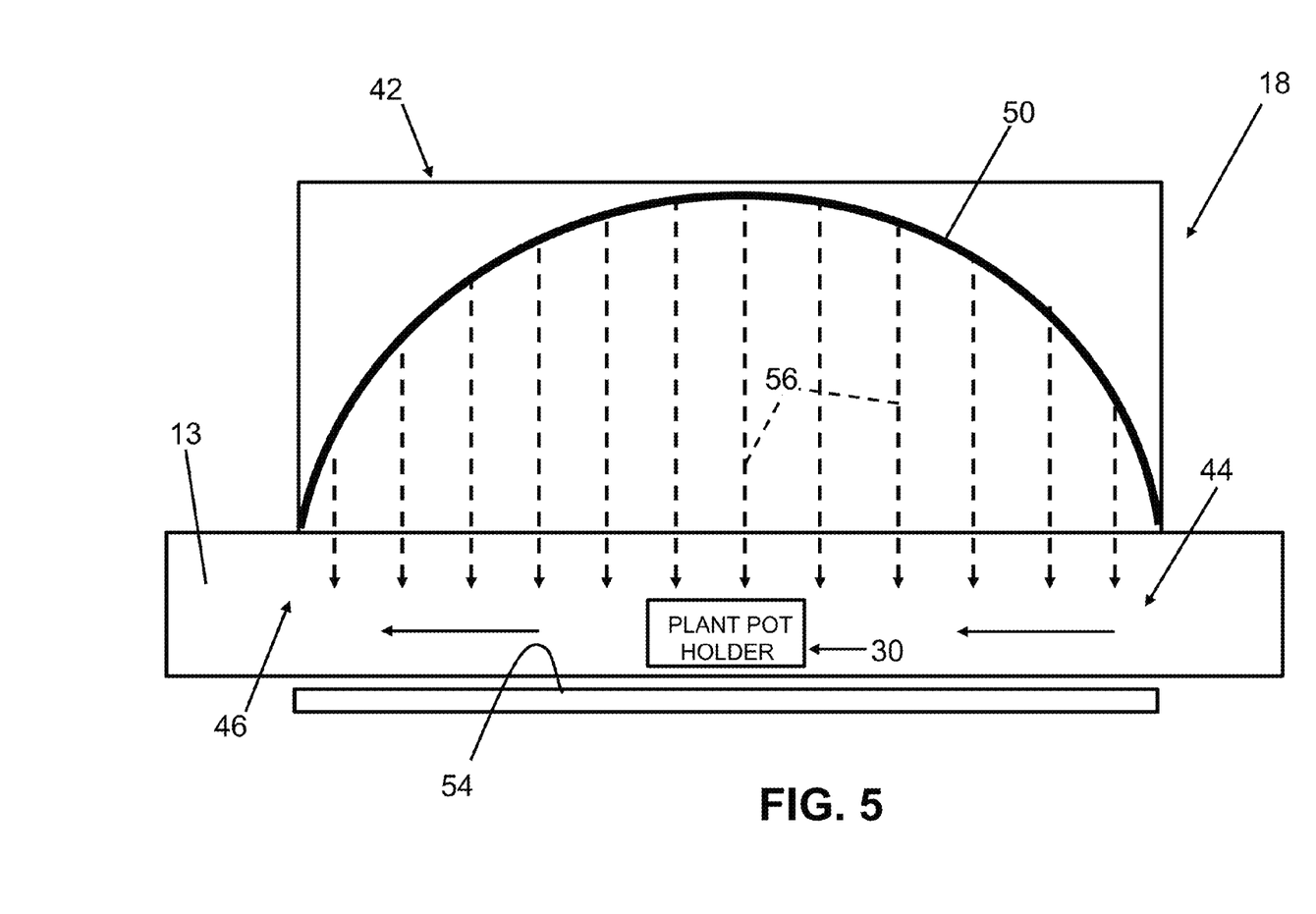
FIG. 5 illustrates additional details of the imaging booth of FIG. 4.

Referring now to FIGS. 4 and 5, the illustrating imaging booth 18 includes a housing 42 having an entrance opening 44 and an exit opening 46 to permit pot holders 30 to enter and exit the imaging booth 18 on the conveyor belt 13. In an illustrated embodiment, a gate 47 is controlled by conveyor controls 14 and computer 16 to meter loading of the plant pots 30 from loading station 12 onto conveyor belt 13. In an illustrated embodiment, an automated door 48 is movable by an actuator 49 to open and close the entrance opening 44 of housing 42 of imaging booth 18. An arcuate wall 50 located inside housing 42 is provided with an array of lights to illuminate the plant 38 passing through the imaging booth 18 in pot holder 30. In FIG. 4, a portion of housing 42 behind arcuate wall 50 is shown in dotted lines.

In an illustrated embodiment of FIGS. 4 and 5, the arcuate wall 50 is formed by a flexible panel of LED lights, such as rope lights, forming the concave, semicircular arcuate wall 50 surrounding the plant 38 located within plant pot holder 30. A generally planar interior side wall 54 of housing 42 is located on an opposite side of conveyor belt 13 from the arcuate light wall 50. As diagrammatically illustrated in FIG. 5, light from the arcuate wall 50 is emitted from the plurality of LEDs or other light sources in the direction of arrows 56 generally perpendicular to the wall 54. An interior surface of a ceiling 51 of housing 42 also has a panel of LED lights or other light sources directed downwardly toward the plant holder 30 on conveyor belt 13. The light sources surrounding the plant 38 on the arcuate wall 50 and ceiling 51 substantially reduce shadows in the images of plants taken by camera 52.

A high resolution camera 52 is located on ceiling 51 above conveyor belt 13 at a central portion of housing 42. Computer 16 controls conveyor controls 14, gate 47 and actuator 49 of movable door 48 so that a single plant 38 within a plant pot holder 30 is moved on conveyor belt 13 to a central portion of the imaging booth 18 as illustrated in FIGS. 4 and 5. Computer 16 then uses conveyor controls 14 to stop the conveyor belt 13. Camera 52 is then used to take images of the plant 38 within imaging booth 18 as illuminated by the LEDs on arcuate wall 50 and ceiling 51. Images from camera 52 are processed by computer 16 using conventional image processing software.

In an illustrated embodiment, the plants 38 are bathed in a diffuse intense light produced by the panel of flexible LEDs formed to a semicircle surrounding the plant 38 on arcuate wall 50 of the imaging booth 18. The background color within the booth 18 on wall 54 is a preferably blue color that is excluded in later color analysis. The conveyor belt 13 is also blue in color. Images are captured by the camera 52 and stored in a memory of computer 16. Batch image analysis is done using publically available image processing software such as Image J software or WinRhizo software available from Regent Instruments Inc., for example.

Computer 16 then actuates conveyor controls 14, gate 47 and actuator 49 of movable door 48 to move the next plant pot holder 30 on conveyor belt 13 into position within the imaging booth 18. The plant pot holder 30 that was just imaged in booth 18 is moved on conveyor belt 13 toward the scanning booth 22.

The plants 38 in pot holders 30 are then progressed in sequence from booth 18 through a light exclusion tunnel 20 that prevents lighting from the imaging booth 18 from permeating into the hyperspectral booth 22. The scanning booth 22 uses conditioned light. Unconditioned light from the surrounding environment reduces capture quality of spectral signatures from the plant's surface in scanning booth 22.

Figure 6:
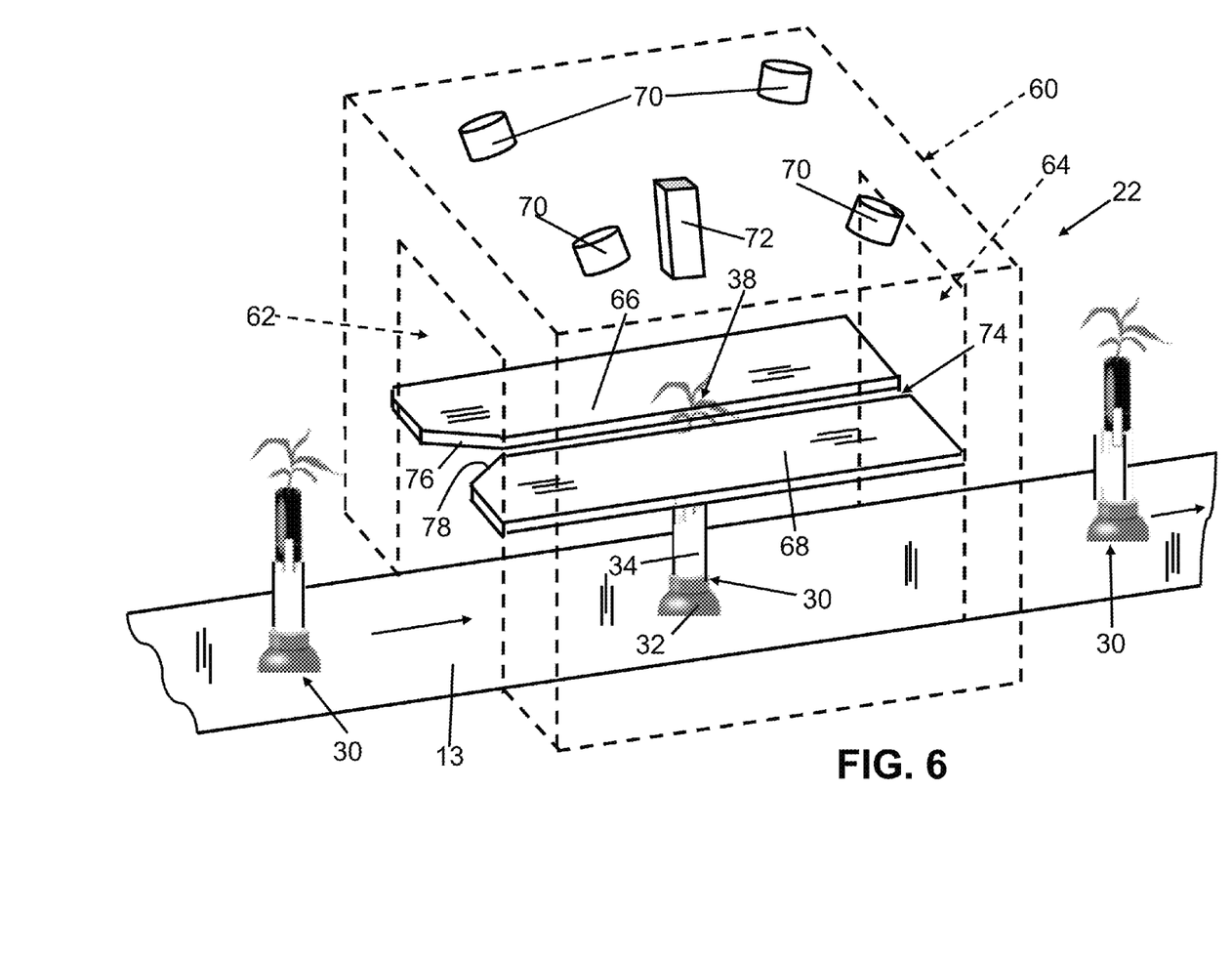
FIG. 6 illustrates details of a spectral scanning booth which captures a reflected spectral signature from intense light shining on the plants as the plants pass through the spectral scanning booth in the plant pot holder on the conveyor belt.

The spectral scanning booth 22 is best illustrated in FIG. 6. Scanning booth 22 includes a housing 60 having an entrance opening 62 and an exit opening 64. Housing 60 is shown in dotted lines in FIG. 6 so that internal components of the scanning booth 22 are visible.

The housing 60 of scanning booth 22 is internally lined with black felt or other suitable material. The blue conveyer 13 within the hyperspectral scanning booth 22 is substantially blocked by shields 66 and 68 supported by housing 60. Four equidistantly spaced high intensity lamps 70 provide intense pure light shining on the surface of the plant 38 positioned within the scanning booth 22 below the lamps 70. Exemplary lamps 70 are available from Analytical Spectral Devices (ASD). Lamps 70 are illustratively coupled to a ceiling within the housing 60 of scanning booth 22. Lamps 70 replicate outdoor solar conditions for the plants 38. An ASD spectroradiometer probe 72 is also mounted within the housing 60 of scanning booth 22 above the plants 38 passing therethrough. The probe 72 collects reflectance, radiance and irradiance measurements from the plants 38. A reflected spectral signature from plants 38 is captured with the computer 16 and analyzed using conventional software. There is a small window in housing 60 for viewing the plants 38 and for use as a maintenance window for viewing the lamps 70 and probe 72.

The shields 66 and 68 are generally parallel to the conveyor belt 13 and extend longitudinally from the entrance opening 62 to the exit opening 64 of housing 60. Shields 66 and 68 are separated from each other by a longitudinally extending gap 74 to permit the plant 38 to pass between the shields 66 and 68. In an illustrated embodiment, the gap 74 has a dimension of about three inches (7.6 cm). Lead-in ramp surfaces 76 and 78 on shields 66 and 68, respectively, help guide the plant 38 into the slot 74. Preferably, a stalk of the plant 38 extends through the slot so that leaves of the plant 38 are located above the shields 66 and 68 in the lighted region of booth 22 for scanning by the probe 72. The shields 66 and 68 are also covered with black felt or other suitable material to improve the effectiveness of probe 72.

Plants 38 exiting the scanning booth 22 move to the gravity fed unloading station 24. In an illustrated embodiment, the computer 16 controls conveyer controls 14, the camera 52 within imaging booth 18 and the probe 72 within scanning booth 22. For example, when the conveyer 13 stops with plants 38 in the imaging booth 18 and scanning booth 22, computer 16 automatically takes the pictures with the camera 52 of imaging booth 18 and automatically reads the information from the probe 72 within scanning booth 22. In another embodiment, the illustrated system 10 is completely automated using a robotic arm for loading plants from an adjacent platform to the gravity fed loading station 12 and for unloading plants from the gravity fed unloading station 24.

While embodiments of the present disclosure have been described as having exemplary designs, the present invention may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this invention pertains.

The invention claimed is:

1. An apparatus for taking images of a plant located within a plant container moving on a conveyor belt, the apparatus comprising:
   an imaging housing having an interior region, an entrance opening and an exit opening to permit the plant container to enter and exit the housing on the conveyor belt, respectively, the imaging housing having a generally planar wall located on a first side of the conveyor belt and an arcuate wall located on a second, opposite side of the conveyor belt, the arcuate wall having a concave shape directed toward the generally planar wall;
   a scanning housing having an interior region, an entrance opening and an exit opening to permit the plant containers to enter and exit the housing on the conveyor belt passing through the scanning housing, the interior region of the scanning housing being spaced apart from the interior region of the imaging housing;
   a plurality of lights located on the arcuate wall of the imaging housing to illuminate the plant in the plant container located on the conveyor belt in front of the generally planar wall; and
   a camera located in the imaging housing above the conveyor belt to capture images of the illuminated plant in the plant container located on the conveyor belt;
   at least one high intensity lamp located in the interior region of the scanning housing above the conveyor belt to illuminate the plant located in the plant container on the conveyor belt;

a spectroradiometer probe located in the interior region of the scanning housing above the conveyor belt to capture a reflected spectral signature from the illuminated plant;

first and second shields located in the scanning housing above the conveyor belt and below the at least one high intensity lamp and the probe, the first and second shields being configured to obscure the conveyor belt from the probe, wherein a stalk of the plant extends through a slot between the first and second shields so that leaves of the plant are located above the first and second shields for illumination by the at least one high intensity lamp and for scanning by the probe; and a light excluding tunnel disposed along the conveyor belt between the imaging housing and the scanning housing, the light excluding tunnel operable to prevent light from the plurality of lights in the imaging housing from influencing the camera located in spectroradiometer probe in the scanning housing.

2. The apparatus of claim 1, further comprising a door located adjacent the entrance opening of the imaging housing, the door being moveable from an open position to permit the plant container to enter the imaging housing on the conveyor belt through the entrance opening of the imaging housing and a closed position to block the entrance opening of the imaging housing.

3. The apparatus of claim 1, wherein the conveyor belt and the generally planar wall within the imaging housing are blue in color to improve plant images captured by the camera.

4. The apparatus of claim 1, wherein the lights are LEDs.

5. The apparatus of claim 4, wherein the lights are formed by a plurality of LED light ropes coupled to the arcuate wall.

6. The apparatus of claim 1, wherein the arcuate wall has a semi-circular shape.

7. The apparatus of claim 1, wherein the imaging housing has a ceiling located above the arcuate wall and the generally planar wall, and further comprising a plurality of lights located on the ceiling of the imaging housing to further illuminate the plant located in the plant container on the conveyor belt.

8. The apparatus of claim 7, wherein the plurality of lights on the arcuate wall and the ceiling are LEDs arranged to illuminate the plant in the plant container located on the conveyor belt.

9. The apparatus of claim 1,
wherein the imaging housing and the scanning housing are arranged such that a respective plant container passes through the imaging housing prior to the scanning housing.

10. The apparatus of claim 1, wherein the at least one high intensity lamp comprises a plurality of spaced apart lamps coupled to a ceiling of the scanning housing.

11. The apparatus of claim 1, wherein the probe collects reflectance, radiance and irradiance measurements from the plant.

12. The apparatus of claim 1, further comprising a computer coupled to the probe, and wherein the reflected spectral signature from plant captured by the probe is analyzed by the computer.

13. The apparatus of claim 1, further comprising a window formed in the scanning housing to permit viewing of the plant, the at least one lamp and the probe from outside the scanning housing.

14. The apparatus of claim 1, wherein the first and second shields are aligned generally parallel to the conveyor belt.

15. The apparatus of claim 14, wherein the first and second shields extend longitudinally from the entrance opening to the exit opening of scanning housing.

16. The apparatus of claim 14, wherein the first and second shields are separated from each other by a longitudinally extending gap forming the slot.

17. The apparatus of claim 1, wherein the first and second shields each include a lead-in ramp surface located adjacent the entrance opening of the scanning housing, the lead-in ramp surfaces of the first and second shields guiding a portion of the plant into the slot between the first and second shields.

18. The apparatus of claim 1, wherein the interior region of the housing and the first and second shields are black in color to improve the effectiveness of probe.

19. The apparatus of claim 18, wherein the conveyor belt is blue in color, the blue color of the conveyor belt being obscured by the black color of the first and second shields.

20. An apparatus for a plant located in a plant container moving on a conveyor belt, the apparatus comprising:

an imaging housing having an interior region, an entrance opening and an exit opening to permit the plant containers to enter and exit the housing on the conveyor belt passing through a bottom portion of the housing, the imaging housing illuminated by at least one light;

a scanning housing having an interior region, an entrance opening and an exit opening to permit the plant containers to enter and exit the housing on the conveyor belt passing through a bottom portion of the scanning housing, the interior region of the scanning housing being spaced apart from the interior region of the imaging housing;

at least one high intensity lamp located in the interior region of the scanning housing above the conveyor belt to illuminate the plant located in the plant container on the conveyor belt;

a spectroradiometer probe located in the interior region of the scanning housing above the conveyor belt to capture a reflected spectral signature from the illuminated plant;

first and second shields located in the housing above the conveyor belt and below the at least one high intensity lamp and the probe, the first and second shields being configured to obscure the conveyor belt from the probe, wherein a stalk of the plant extends through a slot between the first and second shields so that leaves of the plant are located above the first and second shields for illumination by the at least one high intensity lamp and for scanning by the probe; and a light excluding tunnel disposed along the conveyor belt between the imaging housing and the scanning housing, the light excluding tunnel operable to prevent light from the at least one light in the imaging housing from influencing the camera located in spectroradiometer probe in the scanning housing.

21. The apparatus of claim 20, wherein the at least one high intensity lamp comprises a plurality of spaced apart lamps coupled to a ceiling of the scanning housing.

22. The apparatus of claim 20, wherein the probe collects reflectance, radiance and irradiance measurements from the plant.

23. The apparatus of claim 20, further comprising a computer coupled to the probe, and wherein the reflected spectral signature from plant captured by the probe is analyzed by the computer.

24. The apparatus of claim 20, further comprising a window formed in the scanning housing to permit viewing of the plant, the at least one lamp and the probe from outside the scanning housing.

25. The apparatus of claim 20, wherein the first and second shields are aligned generally parallel to the conveyor belt.

26. The apparatus of claim 25, wherein the first and second shields extend longitudinally from the entrance opening to the exit opening of scanning housing.

27. The apparatus of claim 25, wherein the first and second shields are separated from each other by a longitudinally extending gap forming the slot.

28. The apparatus of claim 20, wherein the first and second shields each include a lead-in ramp surface located adjacent the entrance opening of the scanning housing, the lead-in ramp surfaces of the first and second shields guiding a portion of the plant into the slot between the first and second shields.

29. The apparatus of claim 20, wherein the interior region of the housing and the first and second shields are black in color to improve the effectiveness of probe.

30. The apparatus of claim 29, wherein the conveyor belt is blue in color, the blue color of the conveyor belt being obscured by the black color of the first and second shields.

31. The apparatus of claim 20, wherein:
the imaging housing has a generally planar wall located on a first side of the conveyor belt and an arcuate wall located on a second, opposite side of the conveyor belt, the arcuate wall having a concave shape directed toward the generally planar wall;
the at least one light comprises a plurality of lights located on the arcuate wall to illuminate the plant in the plant container located on the conveyor belt in front of the generally planar wall; and
the apparatus further comprises a camera located in the imaging housing above the conveyor belt to capture images of the illuminated plant in the plant container located on the conveyor belt.

32. The apparatus of claim 20, further comprising a door located adjacent the entrance opening of the imaging housing, the door being moveable from an open position to permit the plant container to enter the imaging housing on the conveyor belt through the entrance opening of the imaging housing and a closed position to block the entrance opening of the imaging housing.

33. The apparatus of claim 31, wherein the conveyor belt and the generally planar wall within the imaging housing are blue in color to improve plant images captured by the camera.

34. The apparatus of claim 20, wherein the at least one light comprises a plurality of LEDs.

35. The apparatus of claim 20, wherein the at least one light comprises a plurality of LED light ropes coupled to the arcuate wall.

36. The apparatus of claim 31, wherein the arcuate wall has a semi-circular shape.

37. The apparatus of claim 31, wherein the imaging housing has a ceiling located above the arcuate wall and the generally planar wall, and further comprising a plurality of lights located on the ceiling of the imaging housing to further illuminate the plant located in the plant container on the conveyor belt.

38. The apparatus of claim 37, wherein the plurality of lights on the arcuate wall and the ceiling are LEDs arranged to illuminate the plant in the plant container located on the conveyor belt.

39. The apparatus of claim 20, wherein the imaging housing and the scanning housing are arranged such that a respective plant container passes through the imaging housing prior to the scanning housing.

* * * * *